(12) United States Patent  
Kang

(10) Patent No.: US 9,462,942 B2  
(45) Date of Patent: Oct. 11, 2016

(54) APPARATUS FOR MEASURING STEREOVISION

(71) Applicant: THE CATHOLIC UNIVERSITY OF KOREA INDUSTRY-ACADEMIC COOPERATION FOUNDATION, Seoul (KR)

(72) Inventor: Hang-Bong Kang, Seoul (KR)

(73) Assignee: THE CATHOLIC UNIVERSITY OF KOREA INDUSTRY-ACADEMIC COOPERATION FOUNDATION, Seoul (KR)

(*) Notice: Subject to any disclaimer, the term of this patent is extended or adjusted under 35 U.S.C. 154(b) by 0 days.

(21) Appl. No.: 14/709,748

(22) Filed: May 12, 2015

(65) Prior Publication Data

US 2015/0320305 A1    Nov. 12, 2015

(30) Foreign Application Priority Data

May 12, 2014    (KR) .................. 10-2014-0056414

(51) Int. Cl.
*A61B 3/08* (2006.01)
*A61B 3/00* (2006.01)
*A61B 3/02* (2006.01)

(52) U.S. Cl.
CPC .............. *A61B 3/08* (2013.01); *A61B 3/0041* (2013.01); *A61B 3/0075* (2013.01)

(58) Field of Classification Search
USPC ................. 351/200–246; 359/466, 471, 472, 359/475–477
See application file for complete search history.

(56) References Cited

U.S. PATENT DOCUMENTS 8,384,769 B1 *   2/2013   Hong .................. H04N 13/004  
                                                     345/6  
8,643,677 B2 *   2/2014   Suzuki ................ H04N 13/007  
                                                     345/635  
2014/0211153 A1   7/2014   Kang

FOREIGN PATENT DOCUMENTS

KR    10-1371772 B1    3/2014

* cited by examiner

*Primary Examiner* — Mohammed Hasan  
(74) *Attorney, Agent, or Firm* — NSIP Law

(57) ABSTRACT

There is provided an apparatus to measure stereovision including a frame body, a 3D display unit, a reflective mirror, an eyepiece, a half mirror, a stage, a plurality of protrusion degree markers, a target, and a target driving unit. A reflection angle of the half mirror is adjusted such that an imaginary image of an object having a protrusion degree of 0 in the 3D image reflected on the half mirror is located above the protrusion degree marker having a protrusion degree of 0, the imaginary image being seen through the eyepiece. The target driving unit is controlled such that the target corresponds to an imaginary image of an object of a 3D image having a particular protrusion degree. The stereovision of a tester is evaluated based on a protrusion degree marker to which the target is adjacent among the protrusion degree markers.

4 Claims, 4 Drawing Sheets

APPARATUS FOR MEASURING STEREOVISION

CROSS-REFERENCE TO RELATED APPLICATION

This application claims the benefit under 35 USC 119(a) of Korean Patent Application No. 10-2014-0056414 filed on May 12, 2014 in the Korean Intellectual Property Office, the entire disclosure of which is incorporated herein by reference for all purposes.

TECHNICAL FIELD

The present invention relates to an apparatus for measuring stereovision and in particular to an apparatus for measuring stereovision to measure a degree in which a tester can perceives the protrusion degree of the object in a 3D image.

BACKGROUND ART

Stereovision is one of the most important factors when a 3D content is perceived. Stereovision is a phenomenon in which two images for a particular object are combined into one image to provide a three-dimensional perception when the two images are viewed in such a manner that a left eye takes a view of a left image and a right eye takes a view of a right image at a visual range (approximately 25 cm).

Recently, a 3D content is in high demand as 3D display devices such as a 3D TV, 3D movies, etc. come into wide use. However, statistics show that about 15% of the population do not perceive or enjoy a three-dimensional effect.

Regarding the stereovision, the protrusion degree (depth degree) for an object in a 3D image is a main factor to perceive a 3D image three-dimensionally. 3D contents makers assign a certain protrusion degree to various objects which are contained in the 3D image, respectively. However, people perceive the protrusion degree differently with regard to objects which are made to have the same protrusion degree and therefore, people cannot perceive the protrusion degree which the maker intended.

Regarding the protrusion degree, a viewer feels dizzy when he sees a 3D image having a high protrusion degree which exceeds a predetermined protrusion degree. A viewer who is sensitive to the protrusion degree may be apt to feel dizzy in case of a normal protrusion degree.

Recently, to overcome the problem, a study is being conducted to control the protrusion degree for the objects in a 3D image. If a viewer adjusts the protrusion degree of the 3D image to a protrusion degree suitable for the viewer, the viewer will be able to see the 3D image more clearly and more three-dimensionally.

Here, if 3D contents are developed for which the protrusion degree can be controlled, it is needed to measure the protrusion degree which each individual perceives. That is, at first, a protrusion degree which an individual perceives compared to a protrusion degree of normal people must be determined. Based on this, the protrusion degree of a 3D content which a viewer is watching will be adjusted.

DISCLOSURE OF THE INVENTION

Technical Problem

The invention is provided to solve the above problems. One object of the invention is to provide a stereovision measuring apparatus which can measures a protrusion degree which a tester perceives with regard to objects displayed in a 3D image.

Another object of the invention is to provide a stereovision measuring apparatus which can measure an interocular distance of a tester, NPA (Near Point of Accommodation) and NPC (Near Point of Convergence).

Technical Solution

The object of the invention is accomplished by an apparatus for measuring stereovision comprising: a frame body having a space therein; a 3D display unit which is arranged on the upper part of the frame body and which display a 3D image downwards through the space; a reflective mirror which is arranged on the lower part of the frame body and which reflects the 3D image displayed from the 3D display unit in a forward direction; an eyepiece which is arranged between the 3D display unit and the reflective mirror on the rear part of the frame body and through which a 3D image is seen; a half mirror by which the 3D image reflected forward by the reflective mirror is penetrated and reflected and which is rotatably installed on the frame body to adjust a reflection angle upward or downward; a stage which is arranged in front of the half mirror, a plurality of protrusion degree markers having a predetermined protrusion degree being arranged on the bottom surface successively with a predetermined distance, a target being installed on the stage to move forward, backward, left and right; and a target driving unit which moves the target forward, backward, left and right; wherein a reflection angle of the half mirror is adjusted such that an imaginary image of an object having a protrusion degree of 0 in the 3D image reflected on the half mirror is located above the protrusion degree marker having a protrusion degree of 0, the imaginary image being seen through the eyepiece; and wherein the target driving unit is controlled such that the target corresponds to an imaginary image of an object of a 3D image having a particular protrusion degree, whereby the stereovision of a tester is evaluated based on a protrusion degree marker to which the target is adjacent among the protrusion degree markers.

Here, the distance from the 3D display unit to the protrusion degree marker having a protrusion degree of 0 is configured to correspond to the distance from the 3D display unit to the eyepiece.

Also, the 3D display unit is pivotably installed on the frame body such that the display angle is adjusted with reference to the upward and downward direction of the 3D image; and the display angle of the 3D display unit is adjusted such that the tilting of the 3D image on the eyepiece which is caused by at least one of the height difference between the half mirror and the eyepiece and the reflection angle of the half mirror is removed.

Further, the reflective mirror is mounted on the frame body in such a manner that the reflective mirror moves forward and backward in order to adjust the reflection height of an 3D image displayed from the 3D display unit.

Advantageous Effect

According to the above aspects, a stereovision measuring apparatus is provided which can measures a protrusion degree which a tester perceives with regard to objects displayed in a 3D image.

Further, an interocular distance of a tester, NPA (Near Point of Accommodation) and NPC (Near Point of Convergence) can be measured.

BEST MODE FOR CARRYING OUT THE INVENTION

Hereinafter, preferred embodiments will be explained in detail referring to attached drawings.

Figure 1:
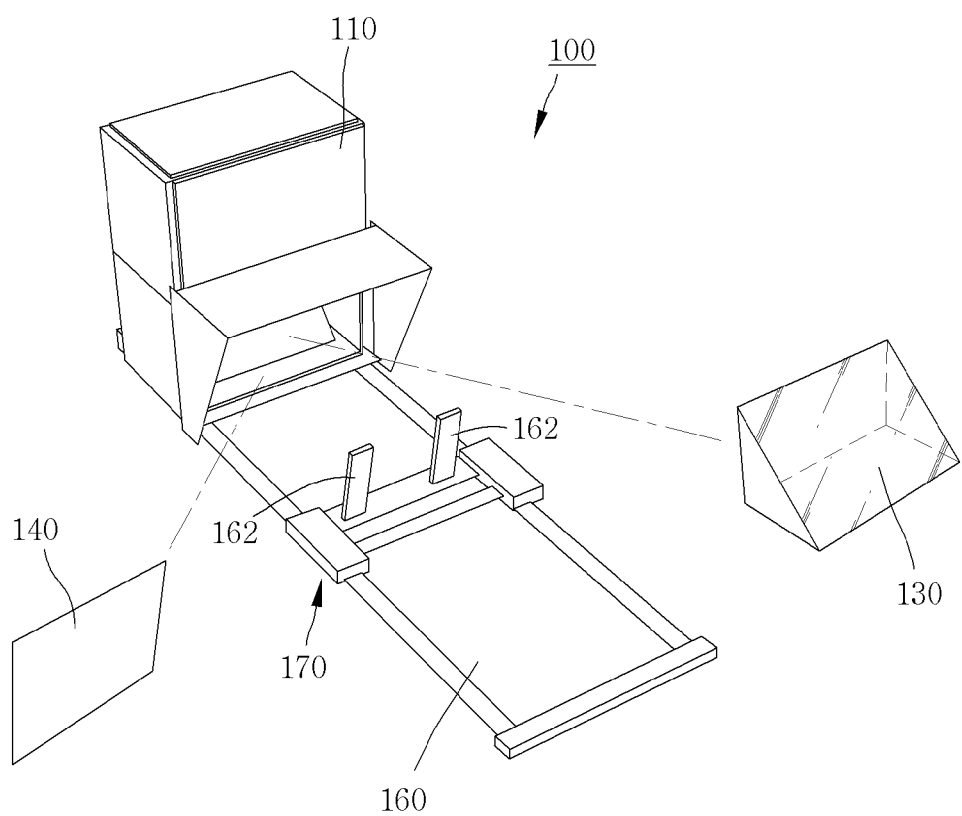
FIGS. 1 and 2 are perspective views of an apparatus for measuring stereovision according to the present invention.
Figure 2:
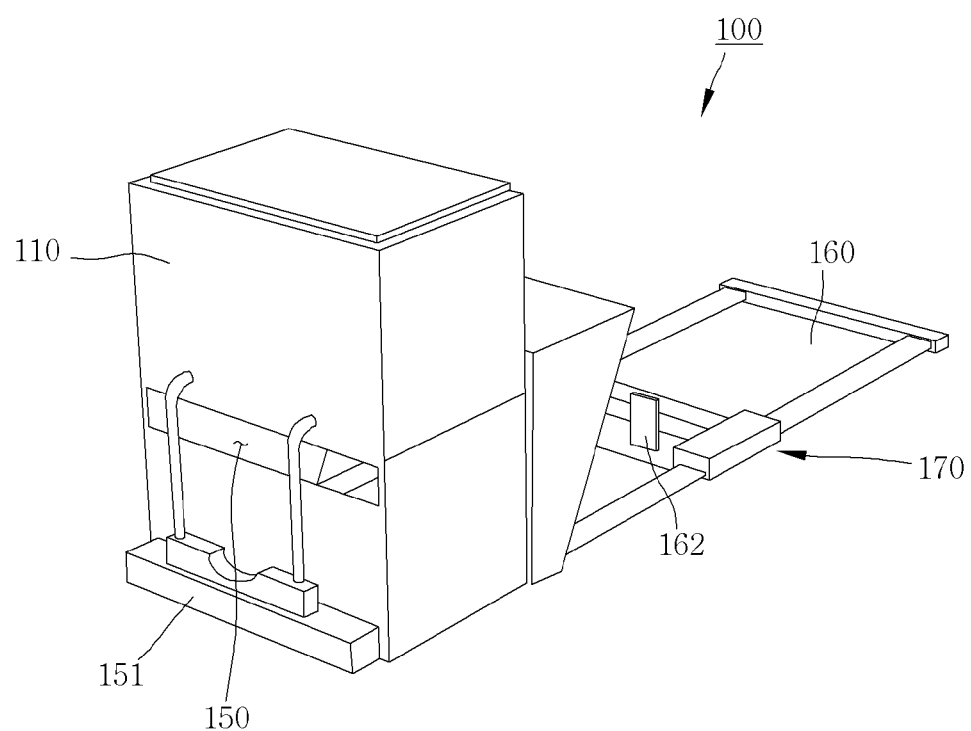
Figure 3:
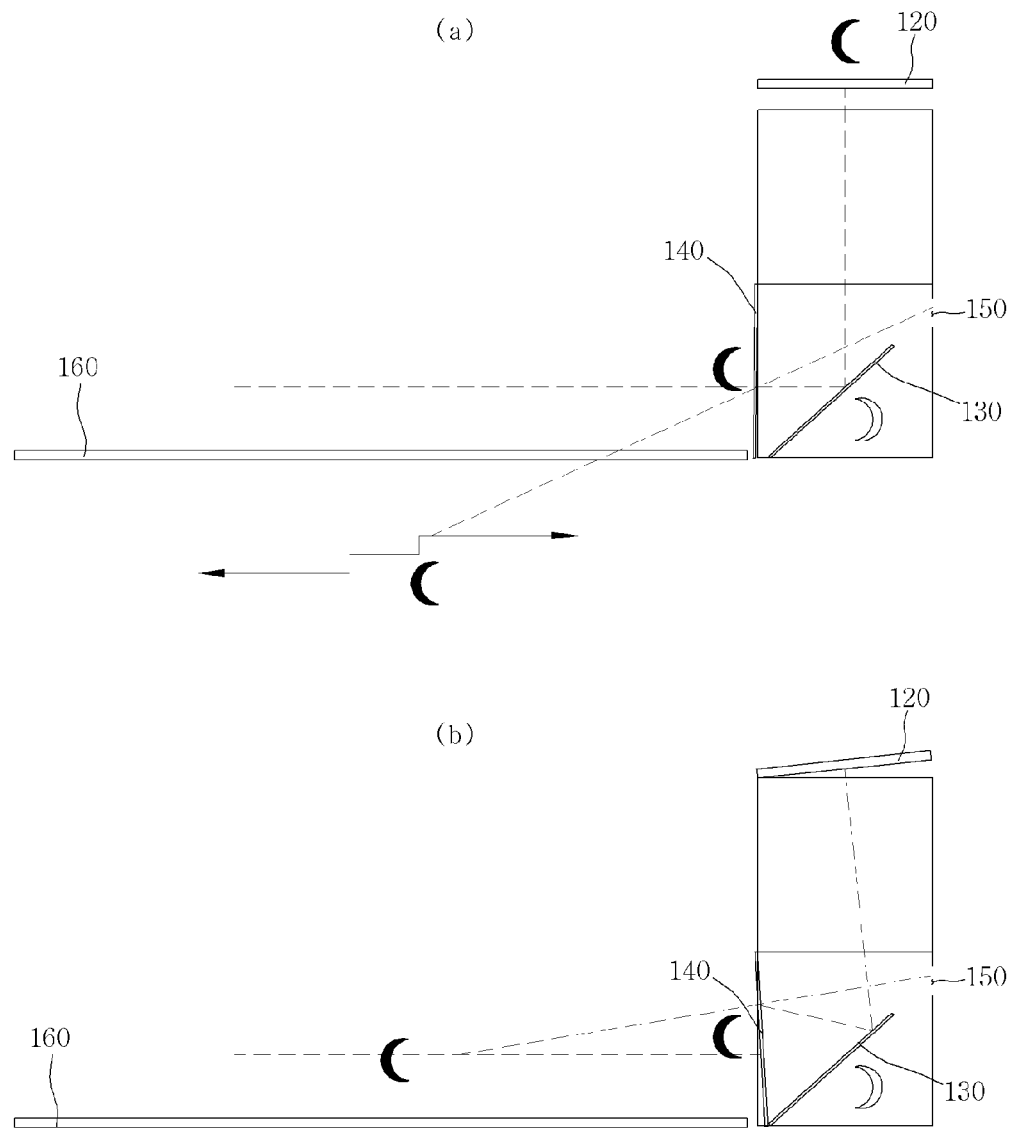
FIG. 3 is a cross-sectional view of an apparatus for measuring stereovision according to the present invention.

FIGS. 1 and 2 are perspective views of an apparatus 100 for measuring stereovision according to the present invention and FIG. 3 is a cross-sectional view of an apparatus 100 for measuring stereovision according to the present invention. Referring to FIGS. 1 and 3, the apparatus 100 comprises a frame body 110, a 3D display unit 120, a reflective mirror 130, an eyepiece 150, a half mirror 140, a stage 160 and a target driving unit 170.

The frame body 110 defines an entire outer shape of the apparatus 100 for measuring stereovision according to the present invention and has an inner space in which a 3D display unit 120, an eyepiece 150 and a half mirror 140 are arranged. The inner space of the frame body 110 forms a light path of a 3D image displayed from the 3D display unit 120.

As shown in FIG. 3, the 3D display unit 120 is installed on the upper part of the frame body 110. The 3D display unit 120 displays a 3D image in a downward direction through the inner space of the frame body 110. A reflective mirror 130 is installed on the lower part of the frame body 110. The reflective mirror 130 reflects a 3D image displayed from the 3D display unit 120 in a forward direction. In the invention, the reflective mirror 130 is arranged at an angle of 45 degree on the lower part of the body frame such that the 3D image displayed from the 3D display unit 120 on the upper part is reflected in a forward direction.

A half mirror 140 is installed in the front of the reflective mirror 130. Here, the lower front part of the frame body 110 is provided with an opening which is open toward the front part and the half mirror 140 is arranged on the opening side of the frame body 110.

Here, the 3D image reflected forwardly by the reflective mirror 130 passes through the half mirror 140 and is reflected by the half mirror 140. That is, some of the 3D image reflected by the reflective mirror 130, i.e. some light, is reflected on the half mirror 140 and then is seen by an eyepiece 150 and the other light passes through the half mirror. Due to the transmission characteristics of the half mirror 140, a tester who is looking at the front through the eyepiece 150 can see the opposite side of the half mirror 140, i.e., the stage 160.

As shown in FIGS. 2 and 3, the eyepiece 150 is arranged on the rear portion of the body frame 110 between the 3D display unit 120 and the reflective mirror 130. In the embodiment, a polarizing filter to see a 3D image is installed on the eyepiece 150 such that a left image and a right image which form a 3D image can be seen distinguishably. Also, as shown in FIG. 2, the eyepiece 150 is provided with a jaw supporting structure 151 to make the face of a tester can be fixed.

The stage 160 is disposed outside the frame body 110 and is connected to the frame body 110 such that it is located in front of the half mirror 140. Further, on the bottom surface of the stage 160, based on a predetermined protrusion degree, a plurality of protrusion degree markers 161a, 161b, 161c and 161d are arranged in consecutive order with a predetermined distance.

Figure 4:
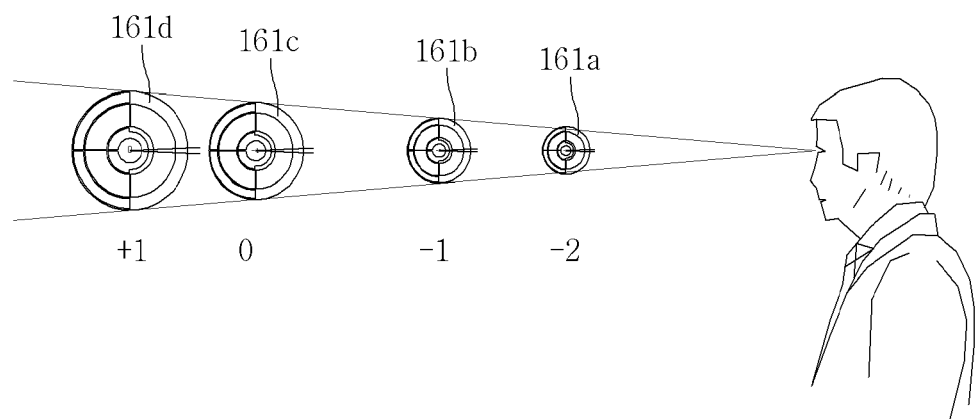
FIG. 4 shows an example of protrusion marker which is displayed on a stage of the stereovision measuring apparatus.

FIG. 4 shows an example of the protrusion degree markers 161a, 161b, 161c and 161d which are arranged on the bottom surface of the stage 160. As shown in FIG. 4, the protrusion markers 161a, 161b, 161c and 161d which represent protrusion degrees of +1, 0, −1 and −2, respectively. Here, the sizes of the protrusion markers 161a, 161b, 161c and 161d become bigger as the markers are farther from the eyepiece 150 such that the sizes are recognized to be the same when a tester see the protrusion degree markers 161a, 161b, 161c and 161d by the eyepiece 150, whereby the sizes of the protrusion markers can be recognized to be the same when a tester see the protrusion degree markers 161a, 161b, 161c and 161d through the eyepiece 150.

Further, the stage 160 is provided with a target 162 which can move forward, backward, left and right. Here, a target driving unit 170 moves the target 162 forward, backward, left and right and in the embodiment, a linear reciprocation structure such as a ball-screw moves a target support on which the target 162 is mounted in order to move the target 162.

Hereinafter, a method for initial-setting a stereovision measuring apparatus 100 according to the present invention will be explained.

As shown in FIG. 3 (a), a 3D image (a black-colored crescent shape) is displayed from the 3D display unit 120 and the 3D image is reflected on the lower reflective mirror 130 toward the front side. At this time, the 3D image reflected on the reflective mirror 130 is mirror-switched (a white-colored crescent shape) and the mirror-switched image is mirror-switched again by the half mirror 140 such that the 3D image is reversed to the original shape (a black-colored crescent shape) and a tester can see the image through the eyepiece 150.

Here, a line of sight of a tester, i.e., the location of the eyepiece 150, is located near the upper part of the half mirror 140 so that the tester can see a screen at the upper part of the half mirror 140. Therefore, as can be seen in FIG. 3 (a), due to an angle of deviation, an imaginary image of the object (OB; see FIG. 5) in the 3D image is recognized to be located below the stage 160, not above the stage 160.

Therefore, as shown in FIG. 3 (b), a reflection angle of the half mirror 140 is adjusted such that an imaginary image of the object (OB) in the 3D image is located above the stage 160. Therefore, the half mirror 140 according to the invention is rotatably mounted on the frame body 110 to adjust the reflection angle.

In one example according to the invention, in case that a 3D image comprising a 3D object (OB) having an protrusion degree of 0 is displayed by the 3D display unit 120, an reflection angle of the half mirror 140 is adjusted such that an imaginary image of the object (OB) in the 3D image is located above the protrusion degree marker 161a, 161b, 161c and 161d having a protrusion degree of 0.

Meanwhile, the stereovision measuring apparatus 100 according to the invention is configured such that the distance from the 3D display unit 120 to the protrusion marker 161a, 161b, 161c and 161d having a protrusion degree of 0 is the same as the distance from the 3D display unit 120 to the eyepiece 150. That is, it is understood that when the protrusion degree is 0, the viewing distance to the protrusion degree marker 161a, 161b, 161c and 161d having a protrusion degree of 0 is the same as the viewing distance of the 3D image displayed from the 3D display unit 120.

Here, as above, if the half mirror 140 is rotated to adjust the reflection angle of the half mirror 140, the tilting of the 3D image occurs during the view through the eyepiece 150 and simultaneously the distance between the 3D display unit 120 and the eyepiece 150 is changed.

To compensate the above change, as shown in FIG. 3 (b), the 3D display unit 120 of the stereovision measuring apparatus 100 according to the invention is rotatably mounted on the frame body 110 such that a display angle is adjusted with reference to the upward and downward direction of a 3D image. By this, the rotation of the 3D display unit 120 removes the tilting of the 3D image which is caused by the reflection angle change of the half mirror 140. Further, the rotation of the 3D display unit 120 causes the eyepiece 150 to be located on the upper part of the half mirror 140, thereby removing the tilting which occurs when a tester views the image.

Also, the distance between the display unit 120 and the eyepiece 150 which occurs by the rotation of the half mirror 140 can be compensated by the manipulation of the reflective mirror 130. The reflective mirror 130 according to the invention is installed on the frame body 110 such that it can move forward and backward. Here, if the reflective mirror 130 moves forward or backward, the reflection height of the 3D image which is displayed from the 3D display unit 120 is adjusted, whereby the viewing distance from the 3D display unit 120 to the eyepiece 150 can be adjusted will be described.

Hereinafter, based on the above arrangement, a method for measuring a tester's perception degree as to a protrusion degree using a stereovision measuring apparatus 100 according to the invention.

First, protrusion degree markers 161a, 161b, 161c and 161d are set based on the protrusion degree in which an ordinary person perceives. For example, based on a person having an average interocular distance of 6.5 cm for ordinary Korean, protrusion degree markers 161a, 161b, 161c and 161d which present the perception degree of the protrusion degree are disposed with a gap as shown in FIG. 4. If a 3D image which comprises an object (OB) of the protrusion degree of −1 is seen based on the protrusion degree markers 161a, 161b, 161c and 161d having a protrusion degree of 0, the protrusion degree markers 161a, 161b, 161c and 161d are set based on pre-studied standard, in such a manner that the corresponding object (OB) is perceived to be protruded with the protrusion degree markers 161a, 161b, 161c and 161d having the protrusion degree of −1 from the protrusion degree markers 161a, 161b, 161c and 161d having the protrusion degree of 0.

With the above setting, when a 3D image having an object (OB) having the protrusion degree of −2 is displayed from the 3D display unit 120 and a tester watches the corresponding object (OB) through the eyepiece 150, a tester can perceives the image as if an imaginary image of the corresponding object (OB) is located at a specific location on the stage 160.

Figure 5:
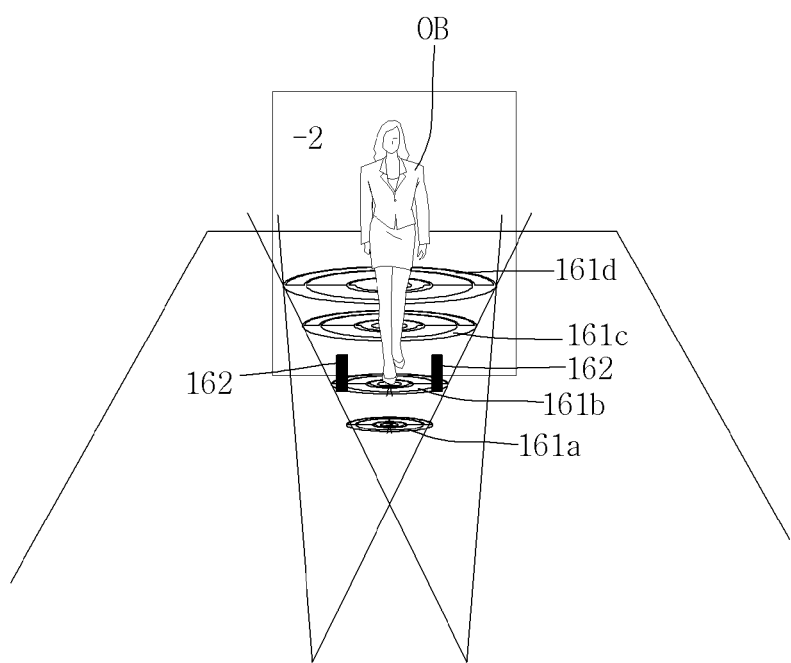
FIG. 5 explains a measuring principle of the stereovision measuring apparatus according to the present invention.

Here, a target driving unit 170 is operated such that a target 162 corresponds to the imaginary image of the object (OB). When the target driving unit 170 moves forward or backward while a tester is watching an object (OB) of the 3D image, a time instant occurs at which the tester can see the target 162 together with the object (OB) clearly, as shown in FIG. 5. The position of the target 162 at this time instant corresponds to the degree of the protrusion which a tester can perceive with regard to the corresponding object (OB).

The above is based on the principle that when a person is looking at a specific object on the specific location, one object having the same distance as the specific object can be seen clearly, but another object having different distance from the specific object is seen vaguely. The protrusion degree of the current object (OB) is measured by finding a time instant when a target 162 is perceived to be located at the same distance while the target 162 is moving forward or backward during the process of looking at the object (OB).

Here, if the location of the target 162 matches the location of the protrusion degree marker 161a, 161b, 161c and 161d which is a standard, a current tester becomes to match the standard. Meanwhile, if the location of the target 162 does not correspond to that of the protrusion markers 161a, 161b, 161c and 161d, a tester can see that the perception of the protrusion degree is different from the standard, and also the tester can see the difference of the degree of perception in accordance with the distance difference between the protrusion degree markers 161a, 161b, 161c and 161d and the target 162.

By performing the above process for the 3D image comprising an object (OB) having protrusion degrees of −1, 0 and +1, it is possible to determine how the current tester has perceived the protrusion degree for an object of the 3D image.

Meanwhile, the stereovision measuring apparatus 100 can be applied to an interocular distance measurement, NPA (Near Point of Accommodation) and NPC (Near Point of Convergence).

First, in case of the interocular distance measurement, when a tester is looking at the front with a face fixed on eyepiece 150, a camera which can photograph two eyes of a tester disposed on the eyepiece 150 in the frame body 110 is installed and markings or gradations are provided on the eyepiece 150 such that the physical interocular distance of the tester can be measured at first from the image taken by the camera.

In case of NPA (Near Point of Accommodation), a transparent pattern part having particular patterns is arranged in front of the reflective mirror 130 in the frame body 110 and a measurement can be performed based on the distance which is determined when the pattern is perceived during the forward movement of the pattern part away from the eyepiece 150.

In case of NPC (Near Point of Convergence), with the setting of the disparity of the object (OB) of the 3D image, a measurement can be performed based on the location where the target 162 becomes vague when the target 162 is located on the corresponding protrusion degree markers 161a, 161b, 161c and 161d.

It is intended that the foregoing description has described only a few of the many possible implementations of the present invention, and that variations or modifications of the embodiments apparent to those skilled in the art are embraced within the scope and spirit of the invention.

LIST OF REFERENCE NUMERALS

100: stereovision measuring apparatus
110: frame body
120: 3D display unit
130: reflective mirror
140: half mirror
150: eyepiece
151: jaw supporting structure 160: stage
161a, 161b, 161c, 161d: protrusion degree marker
162: target
170: target driving unit

The invention claimed is:

1. An apparatus for measuring stereovision comprising:
a frame body having a space therein;
a 3D display unit which is arranged on the upper part of the frame body and which display a 3D image downwards through the space;
a reflective mirror which is arranged on the lower part of the frame body and which reflects the 3D image displayed from the 3D display unit in a forward direction;
an eyepiece which is arranged between the 3D display unit and the reflective mirror on the rear part of the frame body and through which a 3D image is seen;
a half mirror by which the 3D image reflected forward by the reflective mirror is penetrated and reflected and which is rotatably installed on the frame body to adjust a reflection angle upward or downward;
a stage which is arranged in front of the half mirror, a plurality of protrusion degree markers having a predetermined protrusion degree being arranged on the bottom surface successively with a predetermined distance, a target being installed on the stage to move forward, backward, left and right; and
a target driving unit which moves the target forward, backward, left and right;
wherein a reflection angle of the half mirror is adjusted such that an imaginary image of an object having a protrusion degree of 0 in the 3D image reflected on the half mirror is located above the protrusion degree marker having a protrusion degree of 0, the imaginary image being seen through the eyepiece; and
wherein the target driving unit is controlled such that the target corresponds to an imaginary image of an object of a 3D image having a particular protrusion degree, whereby the stereovision of a tester is evaluated based on a protrusion degree marker to which the target is adjacent among the protrusion degree markers.

2. The apparatus according to claim 1, wherein the distance from the 3D display unit to the protrusion degree marker having a protrusion degree of 0 is configured to correspond to the distance from the 3D display unit to the eyepiece.

3. The apparatus according to claim 2, wherein the 3D display unit is pivotably installed on the frame body such that the display angle is adjusted with reference to the upward and downward direction of the 3D image; and wherein the display angle of the 3D display unit is adjusted such that the tilting of the 3D image on the eyepiece which is caused by at least one of the height difference between the half mirror and the eyepiece and the reflection angle of the half mirror is removed.

4. The apparatus according to claim 2, wherein the reflective mirror is mounted on the frame body in such a manner that the reflective mirror moves forward and backward in order to adjust the reflection height of an 3D image displayed from the 3D display unit.

* * * * *